(12) United States Patent
Itotani et al.

(10) Patent No.: US 11,975,448 B2
(45) Date of Patent: May 7, 2024

(54) CONTROL DEVICE AND MASTER-SLAVE SYSTEM

(71) Applicant: SONY GROUP CORPORATION, Tokyo (JP)

(72) Inventors: Yuki Itotani, Tokyo (JP); Hiromasa Masuda, Tokyo (JP); Noriaki Takasugi, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 366 days.

(21) Appl. No.: 17/593,481

(22) PCT Filed: Mar. 12, 2020

(86) PCT No.: PCT/JP2020/010793
§ 371 (c)(1),
(2) Date: Sep. 20, 2021

(87) PCT Pub. No.: WO2020/203138
PCT Pub. Date: Oct. 8, 2020

(65) Prior Publication Data
US 2022/0161414 A1   May 26, 2022

(30) Foreign Application Priority Data

Mar. 29, 2019   (JP) ................ 2019-067047

(51) Int. Cl.
*B25J 3/00* (2006.01)
*A61B 34/35* (2016.01)
*A61B 34/37* (2016.01)

(52) U.S. Cl.
CPC ........... *B25J 3/00* (2013.01); *A61B 34/35* (2016.02); *A61B 34/37* (2016.02)

(58) Field of Classification Search
CPC ........ B25J 3/00; B25J 3/02; B25J 3/04; A61B 34/30; A61B 34/35; A61B 34/37;
(Continued)

(56) References Cited

U.S. PATENT DOCUMENTS

| 2007/0083098 A1 | 4/2007 | Stern et al. |
| 2012/0109377 A1 | 5/2012 | Stern et al. |

(Continued)

FOREIGN PATENT DOCUMENTS

| CN | 102614019 A | 8/2012 |
| CN | 104473693 A | 4/2015 |

(Continued)

OTHER PUBLICATIONS

Translation of JP-2001150368-A (Year: 2001).*

(Continued)

*Primary Examiner* — Russell Frejd
*Assistant Examiner* — Sara J Lewandroski
(74) *Attorney, Agent, or Firm* — CHIP LAW GROUP

(57) ABSTRACT

There is provided a control device including a control unit configured to control an operation offset that indicates a difference between a control reference point for a slave unit and a control reference point for a master unit on the basis of operation magnification indicating a ratio of a movement amount of the master unit to a movement amount of the slave unit, in which the control unit controls the operation offset for two pairs of master unit and slave unit according to a change in the operation magnification in a case where a designated position of a first pair of master unit and a slave unit of the two pairs of master units and the slave units is kept constant.

10 Claims, 13 Drawing Sheets

(58) Field of Classification Search
CPC .... G05B 2219/2228; G05B 2219/2231; G05B 2219/2232; G05B 2219/2238; G05B 2219/1215; G05B 2219/40405; G05B 2219/39122; G05B 2219/40399; G05B 2219/40401; G05B 2219/40402; G05B 2219/40182; G05B 2219/40184; G05B 2219/40187; G05B 2219/40188; G05B 2219/40189; G05B 2219/40192; G05B 2219/40193; G05B 2219/40195; G05B 2219/42188
See application file for complete search history.

(56) References Cited

U.S. PATENT DOCUMENTS

2014/0296870 A1    10/2014  Stern et al.
2016/0135909 A1*   5/2016   Ogawa ..................... B25J 3/04
                                                    606/130
2017/0112368 A1    4/2017   Stern et al.
2019/0307524 A1    10/2019  Popovic

FOREIGN PATENT DOCUMENTS

| | | | |
|---|---|---|---|
| CN | 106214262 A | | 12/2016 |
| CN | 110049742 A | | 7/2019 |
| EP | 3551117 A1 | | 10/2019 |
| JP | 59-047174 A | | 3/1984 |
| JP | 2001-150368 A | | 6/2001 |
| JP | 2001150368 A | * | 6/2001 |
| JP | 2013-017513 A | | 1/2013 |
| KR | 10-2012-0068597 A | | 6/2012 |
| WO | 2018/104252 A1 | | 6/2018 |

OTHER PUBLICATIONS

International Search Report and Written Opinion of PCT Application No. PCT/JP2020/010793, dated Jun. 2, 2020, 08 pages of ISRWO.

* cited by examiner

CONTROL DEVICE AND MASTER-SLAVE SYSTEM

CROSS REFERENCE TO RELATED APPLICATIONS

This application is a U.S. National Phase of International Patent Application No. PCT/JP2020/010793 filed on Mar. 12, 2020, which claims priority benefit of Japanese Patent Application No. JP 2019-067047 filed in the Japan Patent Office on Mar. 29, 2019. Each of the above-referenced applications is hereby incorporated herein by reference in its entirety.

TECHNICAL FIELD

The present disclosure relates to a control device and a master-slave system.

BACKGROUND ART

In recent years, as a surgical system used when performing endoscopic surgery or the like, a master-slave type system (hereinafter, also referred to as a master-slave system) that enables an approach to an affected area without making a large incision in a patient's body has been known. In such a master-slave system, an operator (user) such as a surgeon operates a master unit including an input interface, and a slave unit equipped with medical instruments such as forceps, tweezers, an endoscope, or the like is remotely controlled according to the operation of the master unit by an operator. The slave unit is configured as, for example, an arm device having a surgical instrument provided a tip thereof, and can change a position or posture of a tip device in an abdominal cavity.

In the master-slave system, a display unit (for example, a display or the like) that displays an image of the affected area acquired by the endoscope or the like is used, and an operator performs treatment by operating the master unit while looking at the image displayed on the display unit (for example, see Patent Document 1 below).

CITATION LIST

Patent Document

Patent Document 1: Japanese Patent Application Laid-Open No. 2013-017513

SUMMARY OF THE INVENTION

Problems to be Solved by the Invention

Here, in a case where two pairs of master unit and slave unit are provided in the master-slave system, there was a possibility that each pair of master unit and slave unit cannot not be controlled properly according to a change in a ratio (hereafter, also referred to as operation magnification) of a movement amount of the master unit to a movement amount of the slave unit. For example, in a state where an operating area of the slave unit in the two pairs of master unit and slave unit is approximately the same, in a case where the operation magnification is changed, there is a case where the designated position of at least one of each pair of the master unit and the slave unit changes (that is, at least one of each of the master unit and the slave unit moves). As a result, in the master-slave system used for surgery as described above, operational errors such as the occurrence of an unintended contact with the affected area can be triggered.

Therefore, the present disclosure has been made in view of the above circumstances, and the present disclosure provides a new and improved control device and master-slave system capable of more appropriately controlling each pair of master unit and slave unit according to a change in operation magnification in a case where two pairs of master unit and slave unit are provided in the master-slave system.

Solutions to Problems

According to the present disclosure, there is provided a control device including a control unit configured to control an operation offset that indicates a difference between a control reference point for a slave unit and a control reference point for a master unit on the basis of operation magnification indicating a ratio of a movement amount of the master unit to a movement amount of the slave unit, in which the control unit controls the operation offset for two pairs of master unit and slave unit according to a change in the operation magnification in a case where a designated position of a first pair of master unit and a slave unit of the two pairs of master units and the slave units is kept constant.

Further, according to the present disclosure, there is provided a master-slave system including a slave unit, a master unit used for an operation of the slave unit, and a control unit configured to control an operation offset that indicates a difference between a control reference point for the slave unit and a control reference point for the master unit on the basis of operation magnification indicating a ratio of a movement amount of the master unit to a movement amount of the slave unit, in which the control unit controls the operation offset for two pairs of master unit and slave unit according to a change in the operation magnification in a case where a designated position of a first pair of master unit and slave unit of the two pairs of master units and the slave units is kept constant.

MODE FOR CARRYING OUT THE INVENTION

Figure 1:
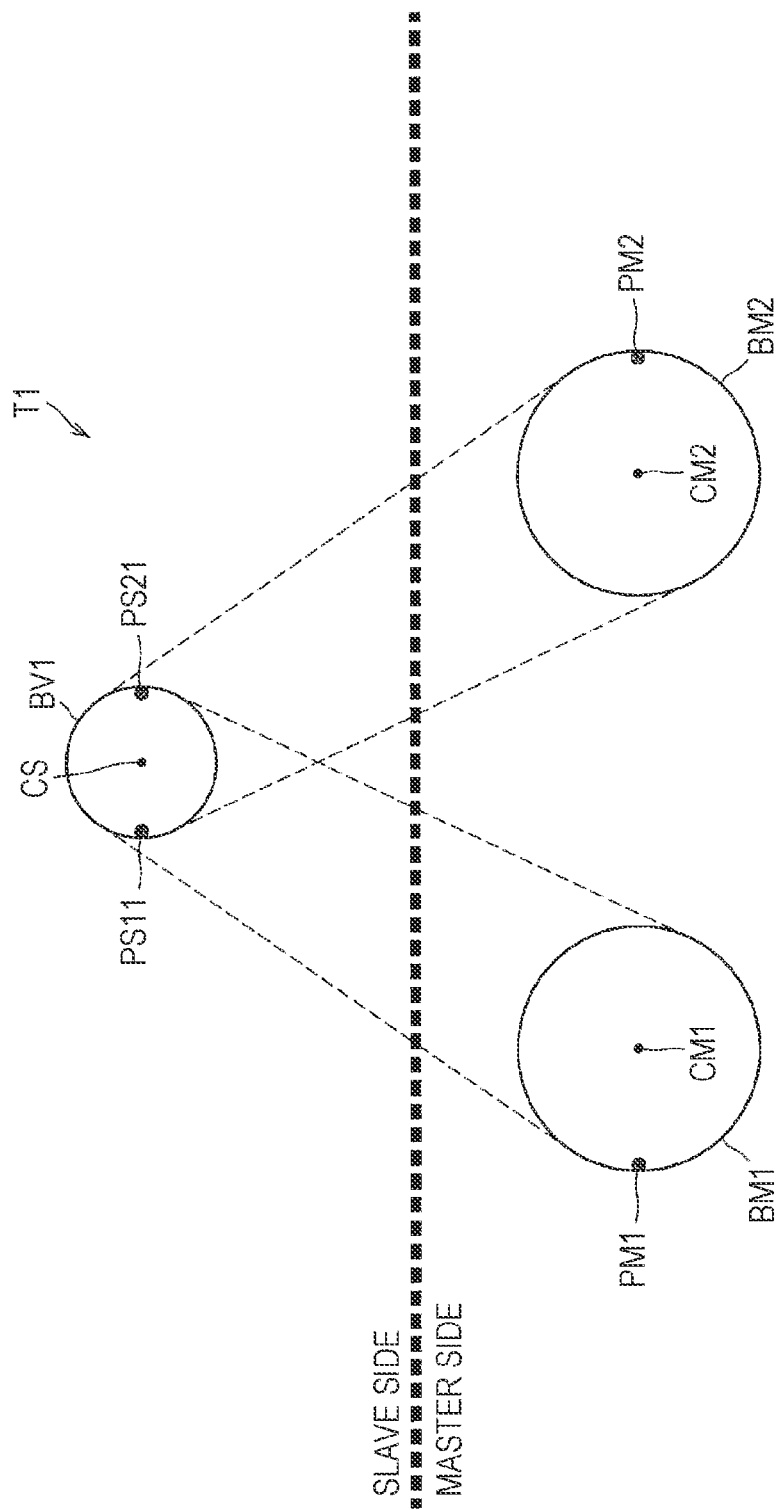
FIG. 1 is a diagram for describing a background that led to a creation of the embodiment of the present disclosure.

Hereinafter, preferred embodiments of the present disclosure will be described in detail with reference to the accompanying drawings. Note that in the present specification and drawings, components having approximately the same functional configuration will be denoted by the same reference numerals, and a redundant description thereof will be omitted.

Note that the description will be made in the following order.
1. Background
2. Embodiment
2.1. System Configuration Example
2.2. Control example by control unit
2.3. Configuration example of control unit
2.4. Example of processing flow of control unit
2.5. Modified Example
2.6. Hardware configuration example of control unit
3. Conclusion

1. BACKGROUND

Before describing the embodiment of the present disclosure, first, the background leading to the creation of the embodiment of the present disclosure will be described.

In recent years, a master-slave system, which is a master-slave type surgical system, has been used in endoscope surgery and the like. Such a master-slave system includes a master unit and a slave unit. The master unit is a configuration for operating the slave unit, and includes an input interface for being operated by an operator such as a surgeon (hereinafter, also referred to as a user). In addition, the slave unit is equipped with forceps, tweezers, medical instruments such as an endoscope, or the like, and is remotely controlled according to a user's operation in the master unit.

In the master-slave system so that a movement amount input in the master unit (hereinafter, also simply referred to as a movement amount related to the master unit) and the movement amount of a medical surgical instrument or the like in the slave unit (hereinafter, simply referred to as a movement amount related to the slave unit). (Also called amount) can be controlled to correspond to each other. For example, the slave unit is controlled according to the movement amount related to the master unit so that the ratio (that is, the operation magnification) of the movement amount of the master unit to the movement amount of the slave unit is constant.

In addition, the master unit and the slave unit each have a control reference point, and a difference between the a control reference point for the slave unit and the control reference point for the master unit is called an operation offset. A range of motion (hereinafter, also simply referred to as a range of motion of the master unit) of the input interface of the master unit and an area (hereinafter, also referred to as an operating area) where a medical surgical instrument or the like of the slave unit can be moved by operating the master unit can be associated on the basis of the operation magnification and the operation offset. Therefore, the larger the operation magnification, the smaller the operating area, and the operating area moves according to the operation offset.

In the master-slave system, it may be possible to dynamically set the operation magnification (that is, change the operation magnification), for example, by setting the operation magnification to be larger, it is possible to expand a work in a smaller area. However, since the range of motion of the master unit is constant regardless of the operation magnification, if the operation magnification is set larger, the operating area becomes smaller, and thus, it is likely to make it difficult to perform a large movement. Further, in a case where the operation magnification is set to be larger, in order to perform a large and quick operation in the slave unit, it is necessary to perform a larger and quick operation in the master unit, and thus, it is likely to make it difficult to perform such an operation. Therefore, in the slave unit, in order to perform a fine operation and a large operation requiring speed at the same time, it is preferable to be able to seamlessly change the operation magnification, for example.

In laparoscopic surgery and the like using the master-slave system, there are many cases where relatively low operation magnification and narrow magnification range operations are performed, while there are fields such as brain surgery in which a relatively high operation magnification and wide magnification range operations are performed, and in such fields, it is especially important to be able to simply change the operation magnification. For example, in the brain surgery and the like, when tying a suture, it is required to perform a precise work with the relatively high operation magnification, while when pulling the tied suture, it is required to make a larger movement. In addition, in a case where changing a medical surgical instrument or the like, it is necessary for the medical surgical instrument to move larger and to deviate from the affected area once, and it is also necessary to lower the image magnification and check the surrounding conditions so that the medical surgical instrument does not come into contact with other affected areas.

Here, in the case where two pairs of master unit and slave unit are provided in the master-slave system, there is a possibility that each pair the master unit and slave unit cannot be appropriately controlled according to a change in operation magnification. For example, in a state where an operating area of the slave unit in the two pairs of master unit and slave unit is approximately the same, in a case where the operation magnification is changed, there is a case where the designated position of at least one of each pair of the master unit and the slave unit changes (that is, at least one of each of the master unit and the slave unit moves). In the following, the event will be described more specifically with reference to FIGS. 1 and 2. Note that a "designated position of the master unit" in this document is a position defined by the master unit, and may be, for example, a position (of the master unit) designated by a user input to the master unit. In addition, a "designated position of the slave unit" is a position defined by the designated position of the master unit, and may be, for example, a position (of the slave unit) designated by a user input to the master unit. That is, it can be the position of the slave unit determined on the master-slave system by the user operating the master unit. Further, the "designated position" is not necessarily limited to the position designated by the user's intention. For example, the "designated position of the master unit" may simply be a position determined by the position of the master unit (the same applies to the "designated position of the slave unit").

FIG. 1 illustrates a center CM1 of a range of motion of a first pair of master unit of the two pairs of master unit and slave unit in state T1, and a boundary BM1 of a range of motion of the first pair of master unit, a center CM2 of a range of motion of the second pair of master unit, and a boundary BM2 of the range of motion of the second pair of master unit. Then, a size of the operating area of the slave unit corresponding to the range of motion of the master unit can change according to the change of the operation magnification. In the state T1 illustrated in FIG. 1, the boundary of the operating areas of the first pair and the second pair of slave units corresponding to the range of motion of the first pair and the second pair of master units is a boundary BV1, and the center of the operating areas of the first pair and the second pair of slave units is a central CS.

Also, the designated position of the first pair of master unit is movable in the range of motion inside the boundary BM1 and is shown as a master position PM1 in the state T1. Further, in the state T1, the first pair of slave unit is controlled so that the designated position of the first pair of slave unit moves to a slave position PS11 corresponding to the master position PM1. In the example of FIG. 1, the master position PM1 is in contact with the boundary BM1, and the slave position PS11 is in contact with the boundary BV1 so as to correspond to the master position PM1. Meanwhile, the designated position of the second pair of master unit is movable in the range of motion inside the boundary BM2 and is shown as a master position PM2 in the state T1. Further, in the state T1, the second pair of slave unit is controlled so that the designated position of the second pair of slave unit moves to a slave position PS21 corresponding to the master position PM2. In the example of FIG. 1, the master position PM2 is in contact with the boundary BM2, and the slave position PS21 is in contact with the boundary BV1 so as to correspond to the master position PM2.

Figure 2:
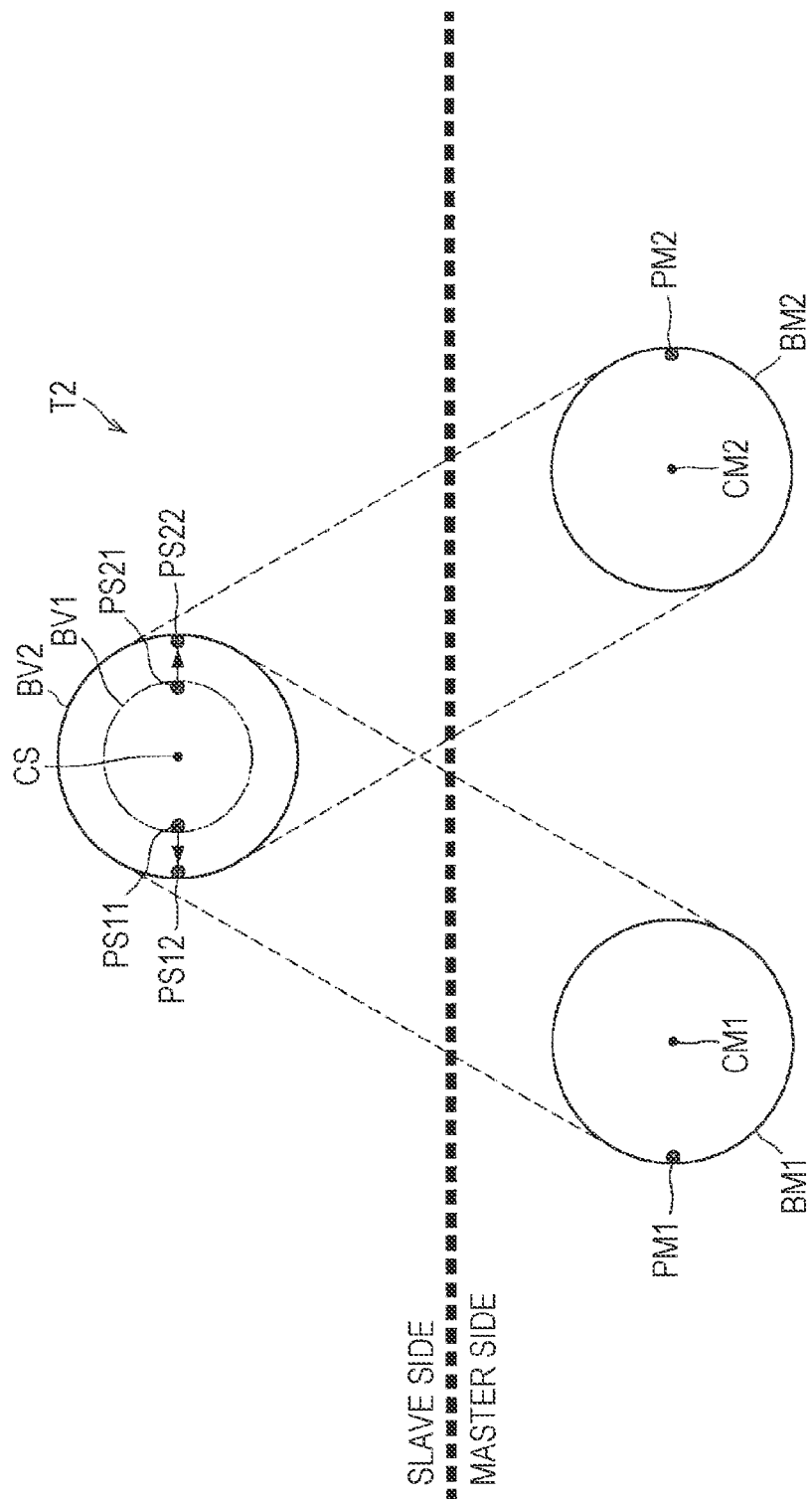
FIG. 2 is a diagram for describing the background that led to the creation of the embodiment of the present disclosure.

FIG. 2 is a diagram illustrating state T2 in which the operation magnification is reduced. By reducing the operation magnification, the boundary of the operating areas of the first pair and the second pair of slave units is extended from the boundary BV1 to the boundary BV2. Due to this change, the designated position of the first pair of slave unit moves from the slave position PS11 to a slave position PS12 according to the master position PM1, and the designated position of the second pair of slave unit moves from the slave position PS21 to a slave position PS22 according to the master position PM2. That is, the first pair and the second pair of slave units move due to the change in the operation magnification. Since the slave unit moves even though the master unit does not move, operational errors such as the occurrence of an unintended contact with the affected area can be triggered.

Note that when the designated positions of the first pair and the second pair of slave units are constant, the designated positions of the first pair and the second pair of master units move according to the designated positions of the first pair and the second pair of slave units, respectively. That is, the first pair and the second pair of master units move according to the change in the operation magnification. As a result, the operation feeling of the master unit changes, and depending on the specifications of the device, a user cannot help but to interrupt the work while the operation magnification changes.

Therefore, the creator of this case has come to create the embodiment according to the present disclosure in view of the above circumstances as a first viewpoint. The control device according to the present embodiment controls the operation offset for two pairs of master unit and slave unit according to the change in the operation magnification in a case where the designated position of the first pair of master unit and slave unit of the two pairs of master unit and slave unit is constant. As a result, the control device according to the present embodiment can remain stationary or control the second pair of master unit and slave unit while making the first pair of master unit and slave unit stationary even during the change in the operation magnification. Then, the control device according to the present embodiment can prevent the operational errors such as the occurrence of the unintended contact with the affected area, and can continue the operation even during the change in the operation magnification. Hereinafter, embodiments of the present disclosure having such effects will be described in detail.

2. SECOND EMBODIMENT

2.1. System Configuration Example

In the above description, the background leading to the creation of the embodiment of the present disclosure has been described. Subsequently, a configuration example of a master-slave system 1 according to the embodiment of the present disclosure will be described.

Figure 3:
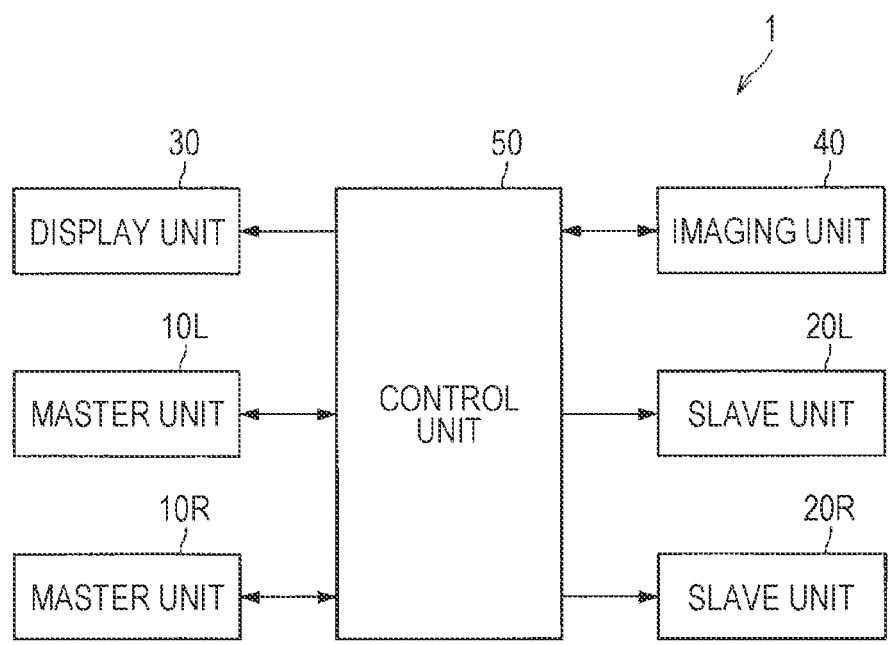
FIG. 3 is a block diagram illustrating a configuration example of a master-slave system according to the present embodiment.

FIG. 3 is a block diagram illustrating the configuration example of the master-slave system 1 according to the present embodiment. As illustrated in FIG. 3, the master-slave system 1 includes a master unit 10L, a master unit 10R, a slave unit 20L, a slave unit 20R, a display unit 30, an imaging unit 40, and a control unit 50. Hereafter, there is a case simply called master unit 10 in the case that refers to both the master unit 10L and the master unit 10R. In addition, there is a case simply called slave unit 20 in the case that refers to both the slave unit 20L and the slave unit 20R. Further, the master-slave system 1 according to the present embodiment will be described assuming a case where a surgical system is used for endoscope surgery and the like, but the type of the master-slave system 1 is not necessarily limited to the surgical system. Note that the control device according to the present embodiment may include at least the control unit 50 in the above configuration.

The master unit 10 is a device on a master side in the master-slave system 1. The master unit 10L can be used to operate the slave unit 20L, and the master unit 10R can be used to operate the slave unit 20R. For example, the master unit 10L may be operated by a user's left hand and the master unit 10R may be operated by a user's right hand. The master unit 10 may be a manipulator (robot having a link mechanism including a passive joint) having one or more joints including a passive joint and a link connected to the joint.

Figure 4:
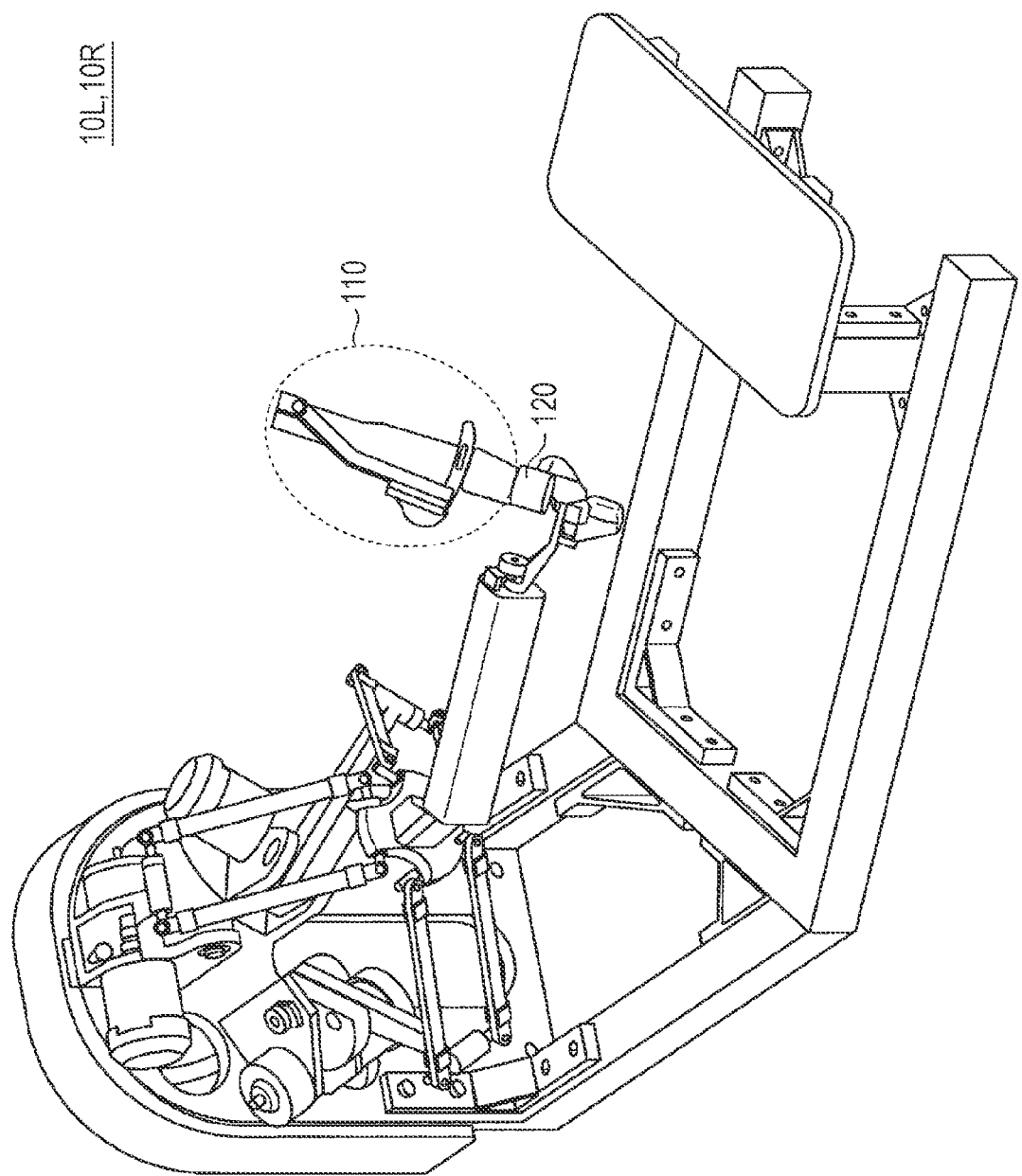
FIG. 4 is a diagram illustrating an example of a master unit according to the present embodiment.

FIG. 4 is a diagram illustrating an example of the master unit 10 according to the present embodiment. In the example illustrated in FIG. 4, the master unit 10 includes an operating body 110 provided on the link connected to the passive joint and a force sensor 120 for measuring a force applied to the operating body 110. Each of the master unit 10L and the master unit 10R can be realized by the device illustrated in FIG. 4. Here, examples of the force sensor 120 according to the present embodiment can include any sensor capable of measuring the force applied to the operating body 110 such as "an inner force sensor of any method such as a method using a strain gauge" or "a tactile sensor of any method such as a method of obtaining a tactile sensation by measuring vibration with a piezoelectric element, microphone or the like". Further, the master unit 10 includes, for example, motion sensors for measuring motions of joints that are provided at positions corresponding to each joint.

In the present embodiment, the operating body 110 is an input interface of the master unit 10, and a user can move (remotely control) the position of the slave unit 20 by operating the position of the operating body 110. In the present specification, there is a case in which the position of the operating body 110 of the master unit 10 is simply referred to as the master position. Further, in the present embodiment, a range of motion of the master unit 10 means a range of motion of the operating body 110, and the range of motion limit of the master unit 10 means the range of motion limit of the operating body 110.

Note that although FIG. 4 illustrates an example in which the operating body 110 provided in the master unit 10 is a stylus type operating device, the operating body 110 according to the present embodiment is not limited to the example illustrated in FIG. 4. Examples of the operating body 110 according to the present embodiment include an operating device having any shape, such as a glove-shaped operating device. Further, the operating body 110 according to the present embodiment may be any operating device that can be applied to a haptic device. Further, the master unit 10 may have a structure capable of exchanging the operating body 110. Note that the configuration of the master unit 10 according to the present embodiment is not limited to the example illustrated in FIG. 4, and may be arbitrary.

The slave unit 20 is a device on a slave side in the master-slave system 1. The slave unit 20L can be controlled by the control unit 50 according to the input operation to the master unit 10L, and the slave unit 20R can be controlled by the control unit 50 according to the input operation to the master unit 10R. For example, the slave unit 20L may be operated by a user's left hand and the slave unit 20R may be operated by a user's right hand. The slave unit 20 is a manipulator (robot having a link mechanism including active joints) having one or more active joints and links connected to the active joints so as to move in response to the input operation to the master unit 10. Further, the slave unit 20 includes, for example, drive mechanisms for driving the active joints that are provided at positions corresponding to each active joint. Examples of the drive mechanism include a motor, a driver, or the like. Such a drive mechanism can be controlled by the control unit 50 described later.

Figure 5:
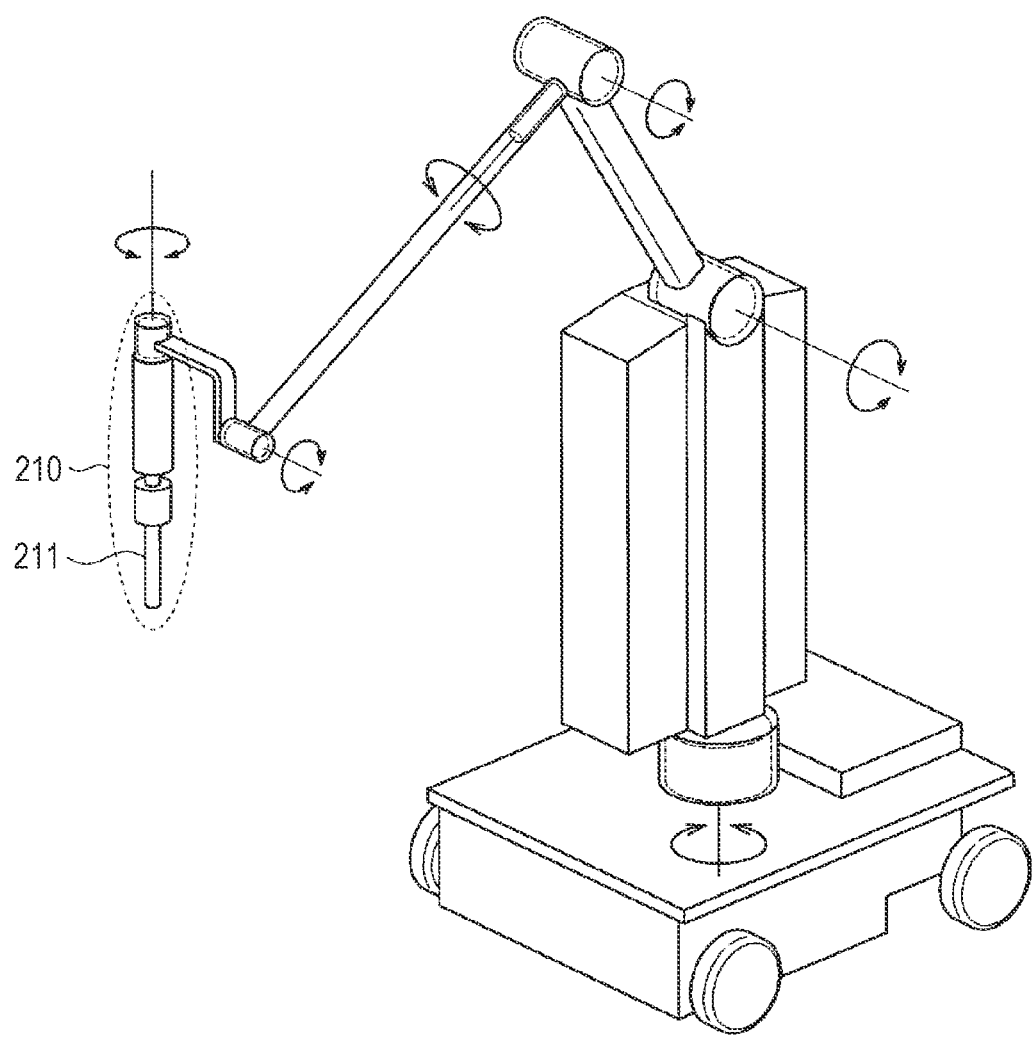
FIG. 5 is a diagram illustrating an example of a slave unit according to the present embodiment.

FIG. 5 is a diagram illustrating an example of the slave unit 20 according to the present embodiment. In the example illustrated in FIG. 5, a tip portion 210, which is a tip portion of an arm of the slave unit 20, includes a contact portion 211 where a surgical instrument contacts a patient, and a user operates the master unit 10 to remotely operate a position the contact portion 211. Each of the slave unit 20L and the slave unit 20R can be realized by the device illustrated in FIG. 5. In the following, there is a case where the position of the contact portion 211 of the slave unit 20 is simply referred to as the slave position. Further, in the present embodiment, the operating area of the slave unit 20 described above may correspond to an area in which the contact portion 211 can be moved by, for example, operating the master unit 10. Note that the example illustrated in FIG. 5 is an example, and the configuration of the slave unit 20 according to the present embodiment is not limited to the example in FIG. 5.

The display unit 30 is a configuration that displays an image output from the control unit 50, which will be described later. The display unit 30 may be a stationary display or a head mounted display (HMD) worn on a user's head.

The imaging unit 40 is a configuration that acquires an image of an affected area by imaging. The imaging unit 40 may be, for example, an endoscope or the like. Further, the imaging unit 40 may be a stereo camera. The imaging unit 40 according to the present embodiment may have a zoom mechanism and may be able to change imaging magnification (zoom magnification). Further, the imaging unit 40 may be supported by, for example, a robot arm (not illustrated), and the position and posture of the imaging unit 40 may be changed by controlling an angle of the joint of the robot arm and the like. The zoom magnification of the imaging unit 40 and the position and posture of the imaging unit 40 can be controlled by the control unit 50 described later.

The control unit 50 is a configuration that controls each of the other configurations included in the master-slave system 1. The control unit 50 is connected to each of the other configurations included in the master-slave system 1 by any communication method. For example, the control unit 50 receives the information measured by the sensor of the master unit 10 from the master unit 10, and acquires the master position (the position of the operating body 110 of the master unit 10) on the basis of the received information. Then, the control unit 50 controls the slave position (contact portion 211 of the slave unit 20) on the basis of the acquired master position, the above-described operation magnification, the operation offset, and the like.

Further, the control unit 50 according to the present embodiment controls the operation offset on the basis of the operation magnification. More specifically, the control unit 50 controls the operation offsets for the two pairs of master unit 10 and slave unit 20 according to a change in operation magnification in a case where the designated position of the first pair of master unit 10 and slave unit 20 (for example, master unit 10L and slave unit 20L) of the two pairs of master unit 10 and slave unit 20 is constant. The control of the operation offset or the like by the control unit 50 will be described in detail below.

2.2. Control Example by Control Unit

In the above, a configuration example of master-slave system 1 according to the present embodiment has been described. Subsequently, a control example by the control unit 50 according to the present embodiment will be described with reference to FIGS. 6 to 9. Hereinafter, as an example, it is assumed that the first pair of master unit 10 and slave unit 20 are the master unit 10L and the slave unit 20L, and the second pair of master unit 10 and slave unit 20 are the master unit 10R and the slave unit 20R.

Figure 6:
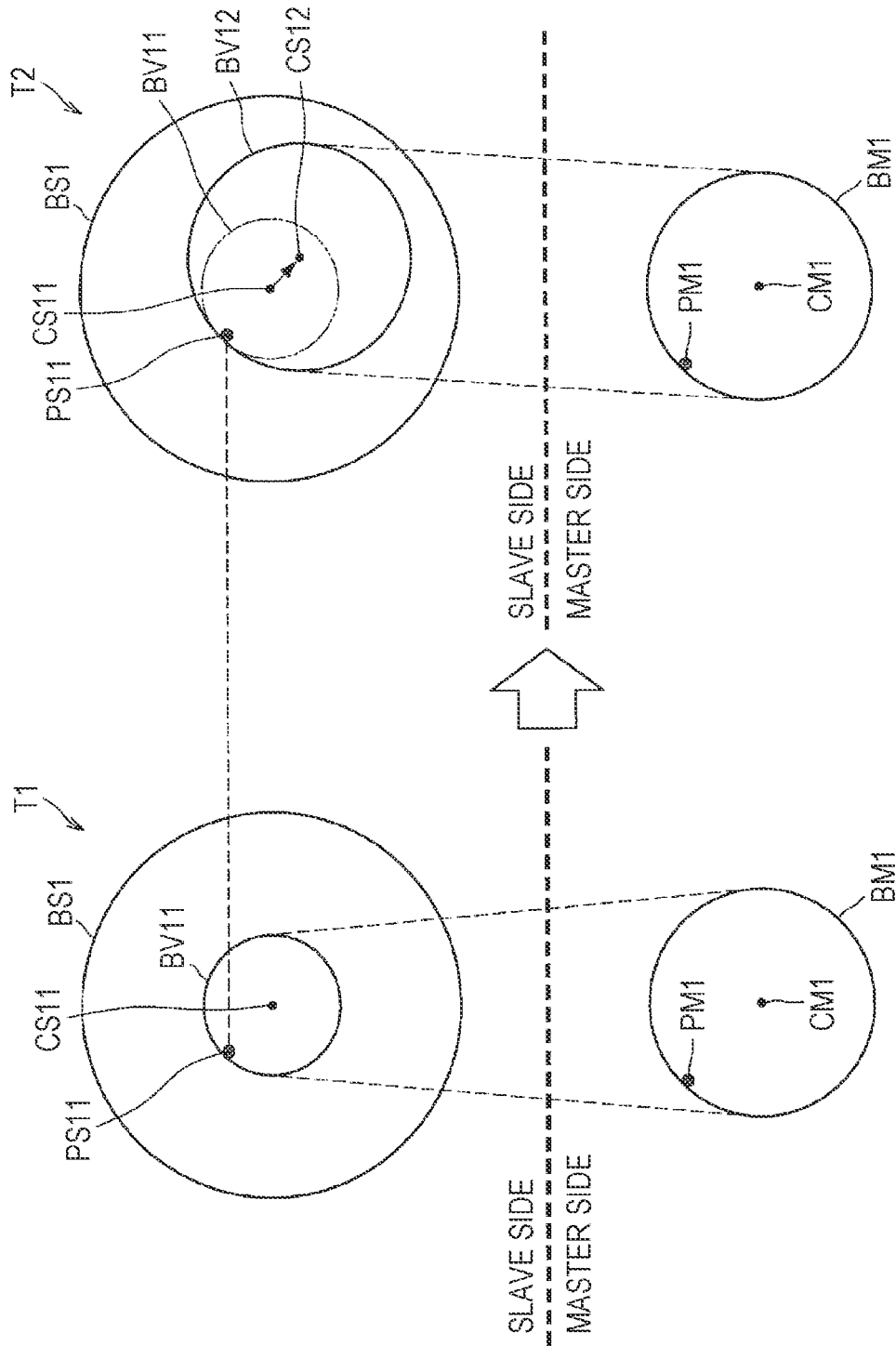
FIG. 6 is a diagram for describing a control example of a first pair of master unit and slave unit according to a change in operation magnification, particularly a reduction in operation magnification.

FIG. 6 is a diagram for describing a control example of a first pair of master unit 10L and slave unit 20L according to the change in the operation magnification, particularly a reduction in operation magnification. In FIG. 6, in the state T1 before the reduction in the operation magnification, the center CM1 of the range of motion of the first pair of master unit 10L and the boundary BM1 of the range of motion of the first pair of master unit 10L, a boundary BV11 of the operating area of the first pair of slave unit 20L corresponding to the boundary BM1, a center CS11 of the operating area of the first pair of slave unit 20L, a master position PM1 which is the designated position of the first pair of master unit 10L, and the slave position PS11 which is the designated position of the first pair of slave unit 20L according to the master position PM1 are illustrated. In addition, a boundary BS1 of a range of motion of the slave unit 20L (particularly contact portion 211) is also illustrated.

In the example of FIG. 6, the state T1 transitions to the state T2 by the reduction control of the control unit 50. Here, the control unit 50 keeps the master position PM1 (designated position of the first pair of master unit 10L) and the slave position PS11 (designated position of the first pair of slave unit 20L) in the transition from the state T1 to the state T2 constant. To this end, the control unit 50 sets the operation offset that can keep the master position PM1 and the slave position PS11 constant on the basis of the operation offset before the change in the operation magnification, the slave position PS11, and the operation magnification before and after the change in the operation magnification. Specifically, the control unit 50 calculates the operation offset after the change in the operation magnification using the following equation 1.

[Equation 1]

$$\vec{r}_0' = \vec{r}_0 + \vec{r} - \frac{a}{a'}\vec{r} \qquad \text{(Equation 1)}$$

$\vec{r}_0$: Operation offset before change in operation magnification (difference between CM1 and CS11)

$\vec{r}_0'$: Operation offset after change in operation magnification (difference between CM1 and CS12)

$\vec{r}$: Slave position in slave coordinate system (difference between CS11, CS12, and PS11)

a: Operation magnification before change in operation magnification a': Operation magnification after change in operation magnification Then, the control unit 50 moves the center of the operating area from the center CS11 to the center CS12 by applying the calculated operation offset after the change in the operation magnification. As a result, as illustrated in FIG. 6, in the state T2, the operating area of the slave unit 20L corresponding to the range of motion of the master unit 10L is larger than the operating area in the state T1, and a boundary BV12 of the operating area in the state T2 will be outside the boundary BV11 in the state T1.

Figure 7:
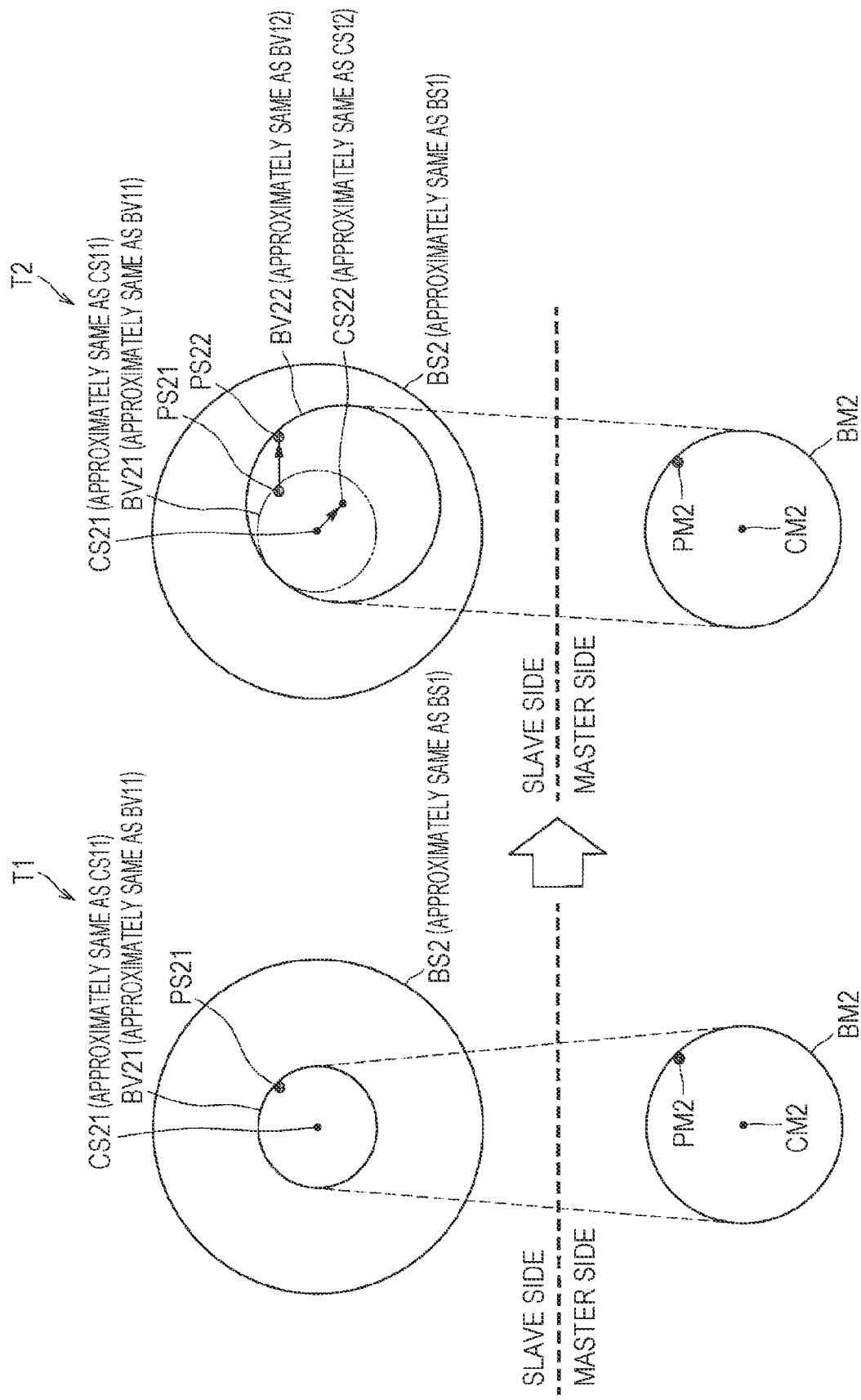
FIG. 7 is a diagram for describing a control example of a second pair of master unit and slave unit according to the change in the operation magnification, particularly the reduction in the operation magnification.

FIG. 7 is a diagram for describing a control example of the second pair of master unit 10R and slave unit 20R according to the change in the operation magnification, particularly a reduction in operation magnification. In FIG. 7, in the state T1 before the reduction in the operation magnification, the center CM2 of the range of motion of the second pair of master unit 10R and the boundary BM2 of the range of motion of the second pair of master unit 10R, a boundary BV21 (approximately the same as the boundary BV11 in FIG. 6) of the operating area of the second pair of slave unit 20R corresponding to the boundary BM2, a center CS21 (approximately the same as the center CS11 in FIG. 6) of the operating area of the second pair of slave unit 20R, a master position PM2 which is the designated position of the second pair of master unit 10R, and the slave position PS21 which is the designated position of the second pair of slave unit 20R according to the master position PM2 are illustrated. In addition, a boundary BS2 (approximately the same as the boundary BS1 in FIG. 6) of the range of motion of the slave unit 20R (particularly the contact portion 211) is also illustrated.

In the case where the state T1 transitions to the state T2 by the reduction control of the control unit 50, the control unit 50 applies the operation offset (that is, operation offset that can keep the master position PM1 and the slave position PS11 related to the first pair constant) calculated above. As a result, the center of the operating area moves from the center CS21 to the center CS22 (approximately the same as the center CS12 in FIG. 6), and the slave position PS21 moves to the slave position PS22. That is, the slave unit 20R moves without the master unit 10R moving. As a result, as illustrated in FIG. 7, in the state T2, the operating area of the slave unit 20R corresponding to the range of motion of the master unit 10R is larger than the operating area in the state T1, and a boundary BV22 (approximately the same as the boundary BV12 in FIG. 6) of the operating area in the state T2 will be outside the boundary BV21 in the state T1.

With the above reduction control, the control unit 50 can move the second pair of slave unit 20R without moving the first pair of master unit 10L and slave unit 20L and the second pair of master unit 10R.

Here, the control unit 50 may change the operation magnification on the basis of the range of motion limit of the master unit 10. More specifically, the control unit 50 may reduce the operation magnification in the case where it is detected that the designated position of the master unit 10 has reached the range of motion limit. For example, as illustrated in the state T1 of FIG. 7, the control unit 50 may reduce the operation magnification in the case where it is detected that the master position PM2 has reached the boundary BM2, which is the range of motion limit of the master unit 10R. In the case where the master position PM2 reaches the boundary BM2, it is considered that the user intends to move the slave unit 20R further away from the center of the operating area. Therefore, the user operates the master unit 10R so that the master position PM2 reaches the boundary BM2 to expand the operating area of the slave unit 20R as illustrated in the state T2 of FIG. 7, and as a result, can move the slave unit 20R further away from the center of the operating area. Also, the user can change the operation magnification using only the master unit 10 without using a dedicated input device.

Further, the control unit 50 may continuously perform the reduction control while it is detected that the designated position of the master unit 10 has reached the range of motion limit. For example, the control unit 50 continues the reduction control while it is detected that the master position PM2 has reached the boundary BM2, which is the range of motion limit of the master unit 10R, as illustrated in state T1 of FIG. 7. As a result, for example, the user continues to operate the master unit 10R so that the master position PM2 reaches the boundary BM2, and as a result, can expand the operating area of the slave unit 20R to the desired size as illustrated in the state T2 of FIG. 7. By applying this function, the control unit 50 can realize the work of pulling the other end of a suture by the desired amount with the second pair of slave unit 20R while fixing an end of the suture with the first pair of slave unit 20L, for example. Needless to say, the application method of the function is not limited thereto.

Furthermore, the control unit 50 controls the image magnification, which is the magnification for the image used for the operation of the slave unit 20, according to the change in the operation magnification. Specifically, the control unit 50 controls the image magnification on the basis of the operation magnification. For example, the control unit 50 controls the operation magnification and the image magnification so that a rate of change of the operation magnification and a rate of change of the image magnification are approximately the same.

Figure 8:
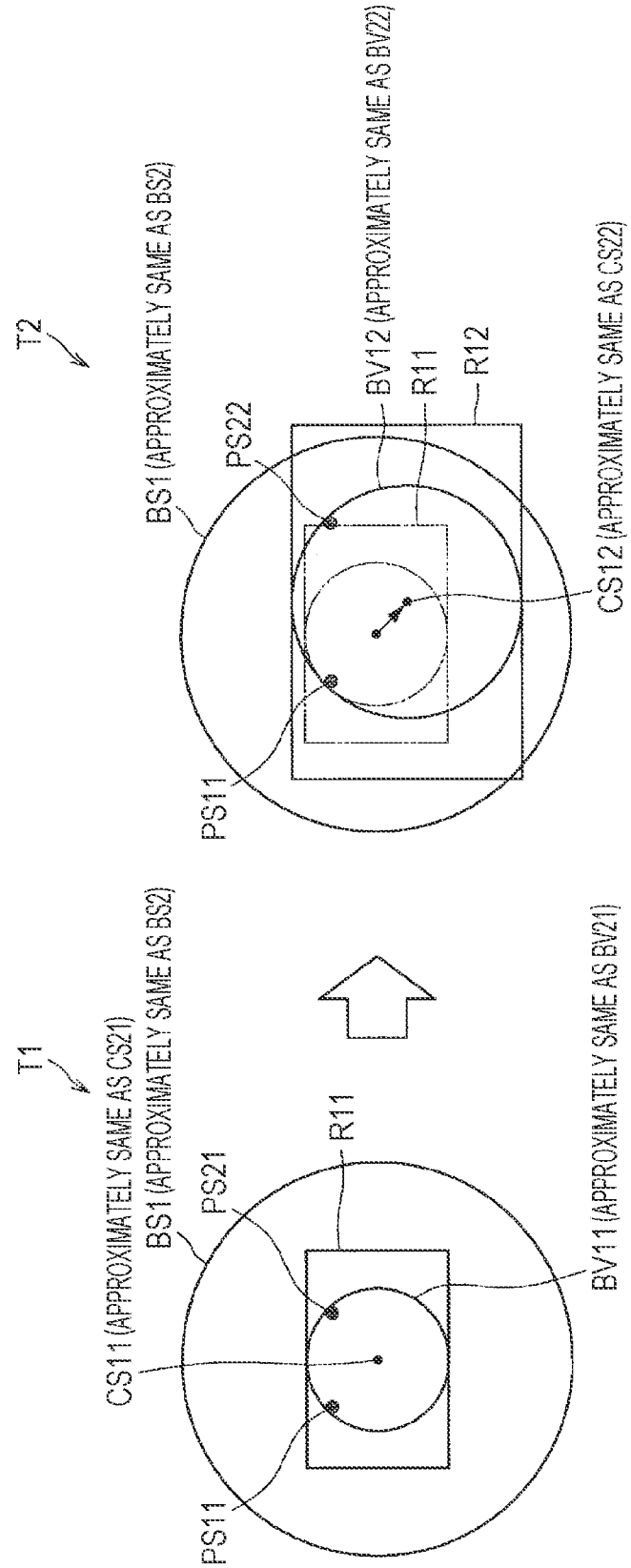
FIG. 8 is a diagram for describing an example of image control according to the change in the operation magnification, particularly the reduction in the operation magnification.

FIG. 8 is a diagram for describing an example of image control according to the change in the operation magnification, particularly the reduction in the operation magnification. FIG. 8 illustrates an imaging range R11 imaged by the imaging unit 40 together with the configurations illustrated in FIGS. 6 and 7 in the state T1. Note that in the present embodiment, the imaging range R11 may also be a display range displayed on the display unit 30. In the example illustrated in FIG. 8, the imaging range R11 in the state T1 includes the entire operating area of the slave unit 20. In addition, in the example illustrated in FIG. 8, the center of the imaging range R11 matches the center CS11 of the range of motion of the slave unit 20.

As the state T1 transitions to the state T2 by the reduction control, the control unit 50 controls the operation magnification and the image magnification so that the rate of change of the operation magnification and the rate of change of the image magnification are approximately the same, thereby changing the imaging range R11 to the imaging range R12. Since the rate of change in the operation magnification and the rate of change in the image magnification are approximately the same, the imaging range R12 similarly includes the entire operating area of the slave unit 20 as in the imaging range R11. As a result, the movement amount of the slave unit 20 displayed on the display unit 30 with respect to the movement amount of the master unit 10 does not change before and after the change in the operation magnification, so that the user can easily perform the operation.

In addition, the control unit 50 further controls an image offset indicating an offset of an image used for the operation of the slave unit 20 according to the control in the operation offset. Specifically, the control unit 50 controls the operation offset and the image offset so that the operating area of the slave unit 20 and the image offset correspond to each other. For example, the control unit 50 controls the operation offset and image offset according to the reduction in the operation magnification so that the movement direction and movement amount of the operating area of slave unit 20 corresponding to the range of motion of master unit 10 and the movement direction and movement amount of the display range related to the image are approximately the same. As a result, as the state T1 illustrated in FIG. 8 transitions to the state T2, the control unit 50 can move the operating area and the imaging range (display range) so as to follow the operating area without the user requiring any additional operation (that is, the center of the imaging range R12 in the state T2 coincides with the center CS12 of the operating area). This allows the user to keep track of the slave position PS11 and the slave position PS22 (that is, contact portion 211 of the slave unit 20) while the operation offset is controlled.

Figure 9:
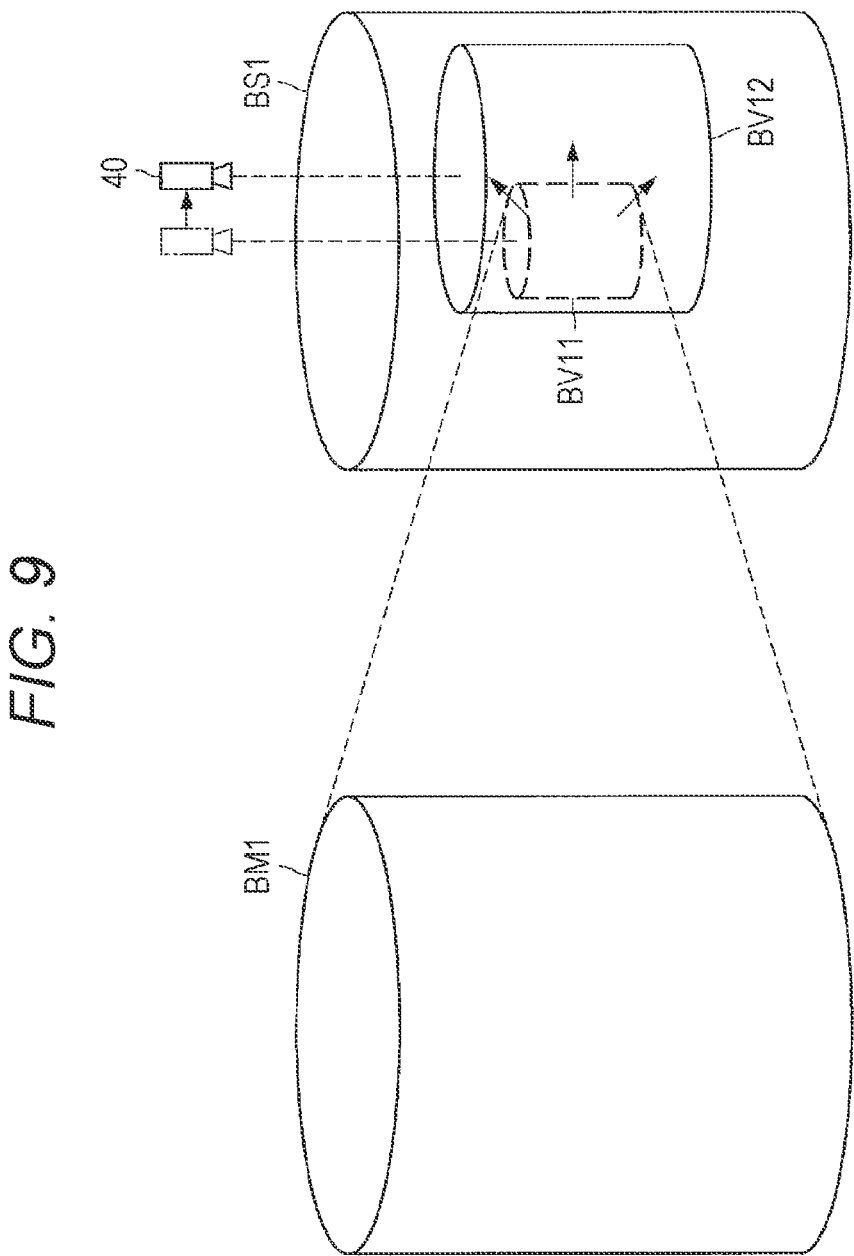
FIG. 9 is a three-dimensional diagram illustrating a range of motion and an operating area when the operation magnification is changed, particularly when the operation magnification is reduced.

FIG. 9 is a three-dimensional diagram illustrating a range of motion and an operating area when the operation magnification is changed, particularly when the operation magnification is reduced. FIG. 9 illustrates the boundary BM1 of the range of motion of the master unit 10, the boundary BS1 of the range of motion of the slave unit 20, and the boundary BV11 of the operating area of the slave unit 20 corresponding to the range of motion of the master unit 10. When the operation magnification is reduced, since the image magnification is also reduced, as illustrated in FIG. 9, the operating area of the slave unit 20 is three-dimensionally expanded, and the boundary BV11 changes to the boundary BV12. In addition, when the operation magnification is reduced, since not only the operation offset but also the image offset is controlled, as illustrated in FIG. 9, the operating area moves, and the imaging unit 40 also moves with approximately the same movement direction and movement amount as the movement direction and movement amount of the operating area.

2.3. Configuration Example of Control Unit

In the above, the control example by the control unit 50 according to the present embodiment has been described. Subsequently, a configuration example of the control unit 50 according to the present embodiment will be described with reference to FIG. 10.

Figure 10:
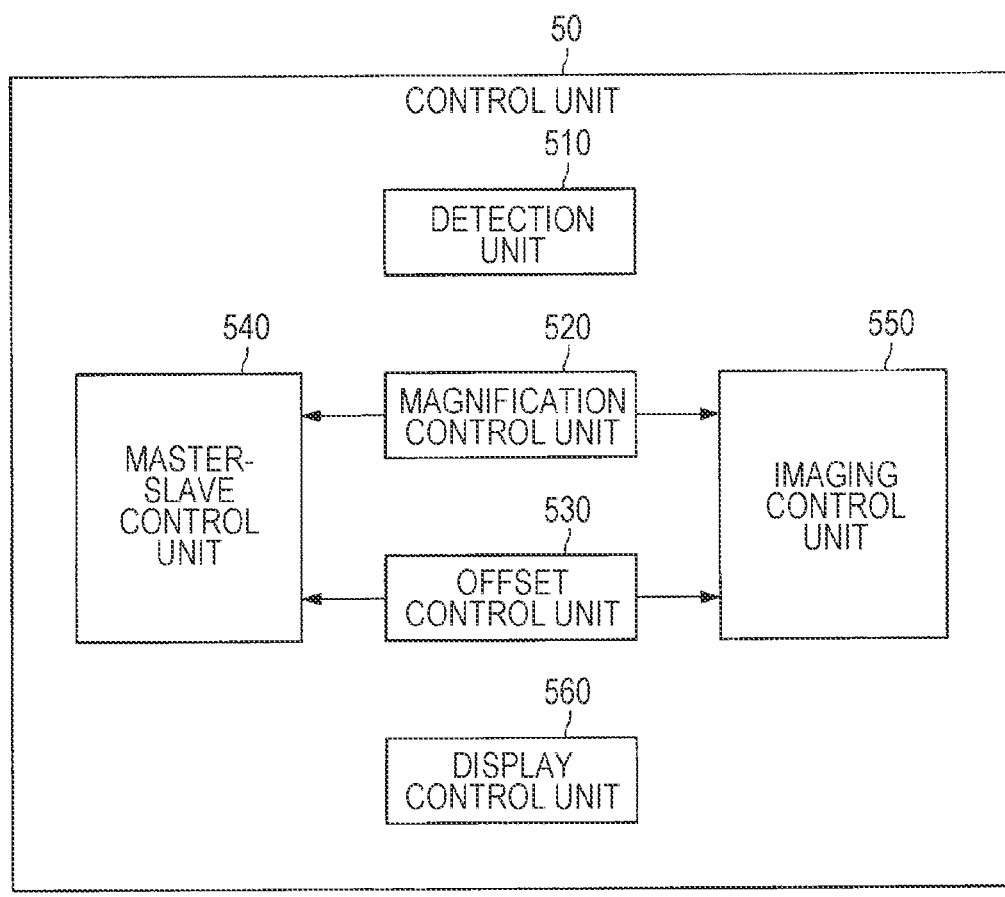
FIG. 10 is a block diagram illustrating a configuration example of a control unit according to the present embodiment.

FIG. 10 is a diagram illustrating a configuration example of the control unit 50 according to the present embodiment. As illustrated in FIG. 10, the control unit 50 includes a detection unit 510, a magnification control unit 520, an offset control unit 530, a master-slave control unit 540, an imaging control unit 550, and a display control unit 560.

The detection unit 510 detects that the designated position of the master unit 10 (including the master unit 10L and the master unit 10R) has reached the range of motion limit on the basis of information linked by communication from the master unit 10. As described above, in the present embodiment, the range of motion limit of the master unit 10 means the range of motion limit of the operating body 110 which is the input interface of the master unit 10. In addition, the range of motion limit of the master unit 10 is a state in which the operating body 110 cannot be moved in a specific direction, or a state close thereto.

For example, in the case where the master position (position of the operating body 110) specified on the basis of the information linked by the communication from master unit 10 is the boundary (boundary BM1 illustrated in FIG. 6 and boundary BM2 illustrated in FIG. 7) of the range of motion of the operating body 110, the detection unit 510 may detect that the designated position of master unit 10 has reached the range of motion limit. The detection unit 510 calculates the master position from, for example, a measured value (for example, a joint angle) of an encoder provided in the joint of the master unit 10. Alternatively, for example, in the case where the master position is within a predetermined distance range from the boundary of the range of motion of the operating body 110, the detection unit 510 may detect that the designated position of the master unit 10 has reached the range of motion limit, Alternatively, in the case which the detection unit 510 has a function of transmitting information indicating that master unit 10 itself has reached the range of motion limit, the detection unit 510 may detect that the designated position of the master unit 10 has reached the range of motion limit on the basis of the information linked by the communication from the master unit 10. Alternatively, in the case where the position of the operating body 110 specified on the basis of the information linked by the communication from the master unit 10 is in contact with or near an end portion of a screen currently displayed on the display unit 30, the detection unit 510 may detect that the designated position of the master unit 10 has reached the range of motion limit. In addition, the detection unit 510 may detect whether or not the designated position of the master unit 10 has reached the range of motion limit on the basis of the distance from the control reference point (center CM1 illustrated in FIG. 6 and center CM2 illustrated in FIG. 7) to the master position. For example, in the case where the distance from the control reference point to the master position is monitored and the distance matches the distance from the control reference point to the boundary of the range of motion, the detection unit 510 may detect that the designated position of master unit 10 has reached the range of motion limit.

The magnification control unit 520 controls the operation magnification and the image magnification. The magnification control unit 520 outputs the operation magnification to the master-slave control unit 540 and the image magnification to the imaging control unit 550. For example, as described with reference to FIGS. 6 to 8, in the case where the detection unit 510 detects that the designated position of the master unit 10 has reached the range of motion limit, the magnification control unit 520 performs the reduction control of the operation magnification and the image magnification. Further, the magnification control unit 520 may continuously perform the reduction control of the operation magnification and the image magnification while the detection unit 510 detects that the designated position of the master unit 10 has reached the range of motion limit. The method for determining operation magnification and image magnification is not particularly limited. For example, the magnification control unit 520 may set the operation magnification and the image magnification specified by the user, set the operation magnification and the image magnification reduced by a predetermined number in the case where the designated position of the master unit 10 reaches the range of motion limit, and set the operation magnification and the image magnification according to the speed or the like of the designated position in the case where the designated position of the master unit 10 reaches the range of motion limit.

Further, the magnification control unit 520 may control the operation magnification and the image magnification approximately at the same time. With such a configuration, the user does not have to perform an additional operation on the displayed image in response to the change in the operation magnification, so the load on the user is reduced.

Further, the magnification control unit 520 may control the operation magnification and the image magnification so that the rate of change of the operation magnification and the rate of change of the image magnification are approximately the same as described above. With such a configuration, the relationship between the size of the operating area and the size of the display range (the same as the imaging range in the present embodiment) is maintained, so the user can operate more comfortably.

The offset control unit 530 controls the operation offset and the image offset. The offset control unit 530 outputs the operation offset to the master-slave control unit 540 and the image offset to the imaging control unit 550. For example, as described with reference to FIGS. 6 to 8, in the case where the detection unit 510 detects that the designated position of the master unit 10 has reached the range of motion limit, the offset control unit 530 performs the control (offset control) of the operation offset and the image offset. Further, the offset control unit 530 may continuously perform the control of the operation offset and the image offset while the detection unit 510 detects that the designated position of the master unit 10 has reached the range of motion limit.

Further, the offset control unit 530 may control the operation offset and the image offset approximately at the same time. With such a configuration, the user does not have to perform an additional operation on the displayed image in response to the change in the operation offset, so the load on the user is reduced.

Also, as described with reference to FIG. 8, the offset control unit 530 may control the operation offset and the image offset so that the movement direction and the movement amount of the operating area of the slave unit 20 corresponding to the range of motion of the master unit 10 and the movement direction and the movement amount of the display range (same as the imaging range in the present embodiment) related to the displayed image are approximately the same. With such a configuration, the relationship between the position of the operating area and the position of the display range (the same as the imaging range in the present embodiment) is maintained, so the user can operate more comfortably.

Also, as described with reference to FIG. 8, the offset control unit 530 may control the operation offset and the image offset so that the center of the operating area and the center (the center of the imaging range in the present embodiment) of the displayed image coincide with each other. With this configuration, the center position of the operating area does not change on the screen that the user is looking at, so it is unlikely that the user will feel uncomfortable.

The master-slave control unit 540 controls the slave unit 20 (master-slave control) on the basis of the master position specified on the basis of the information linked by the communication from the master unit 10, the operation magnification controlled by the magnification control unit 520, and the operation offset controlled by the offset control unit 530.

Note that the master-slave control by the master-slave control unit 540 according to the present embodiment may be similar to the control of the slave device in the existing master-slave method except that the operation magnification controlled by the magnification control unit 520 and the operation offset controlled by the offset control unit 530 are applied, and therefore, a detailed description thereof will be omitted.

The imaging control unit 550 controls the imaging unit 40 (imaging control) on the basis of the image magnification controlled by the magnification control unit 520 and the image offset controlled by the offset control unit 530. For example, in the present embodiment, the image magnification may be the zoom magnification (imaging magnification) of the imaging unit 40, and the imaging control unit 550 can apply the image magnification controlled by the magnification control unit 520 to the imaging control by controlling the zoom magnification of the imaging unit 40. Further, in the present embodiment, the imaging control unit 550 can apply the image offset to the imaging control by moving the imaging unit 40 by driving and controlling the robot arm.

The display control unit 560 generates the display image to be displayed on the display unit 30 on the basis of the captured image acquired by the imaging of the imaging unit 40, and outputs the generated display image to the display unit 30.

The configuration example of the control unit 50 has been described above. Note that the configuration described above with reference to FIG. 10 is merely an example, and the configuration of the control unit 50 is not limited to this example. For example, the control unit 50 does not necessarily have all of the configurations illustrated in FIG. 10, and may have configurations not illustrated in FIG. 10. In addition, the configuration of the control unit 50 can be flexibly modified according to specifications and operation.

2.4. Example of Processing Flow of Control Unit

In the above, the configuration example by the control unit 50 according to the present embodiment has been described. Subsequently, an example of a processing flow of the control unit 50 according to the present embodiment will be described with reference to FIG. 11.

Figure 11:
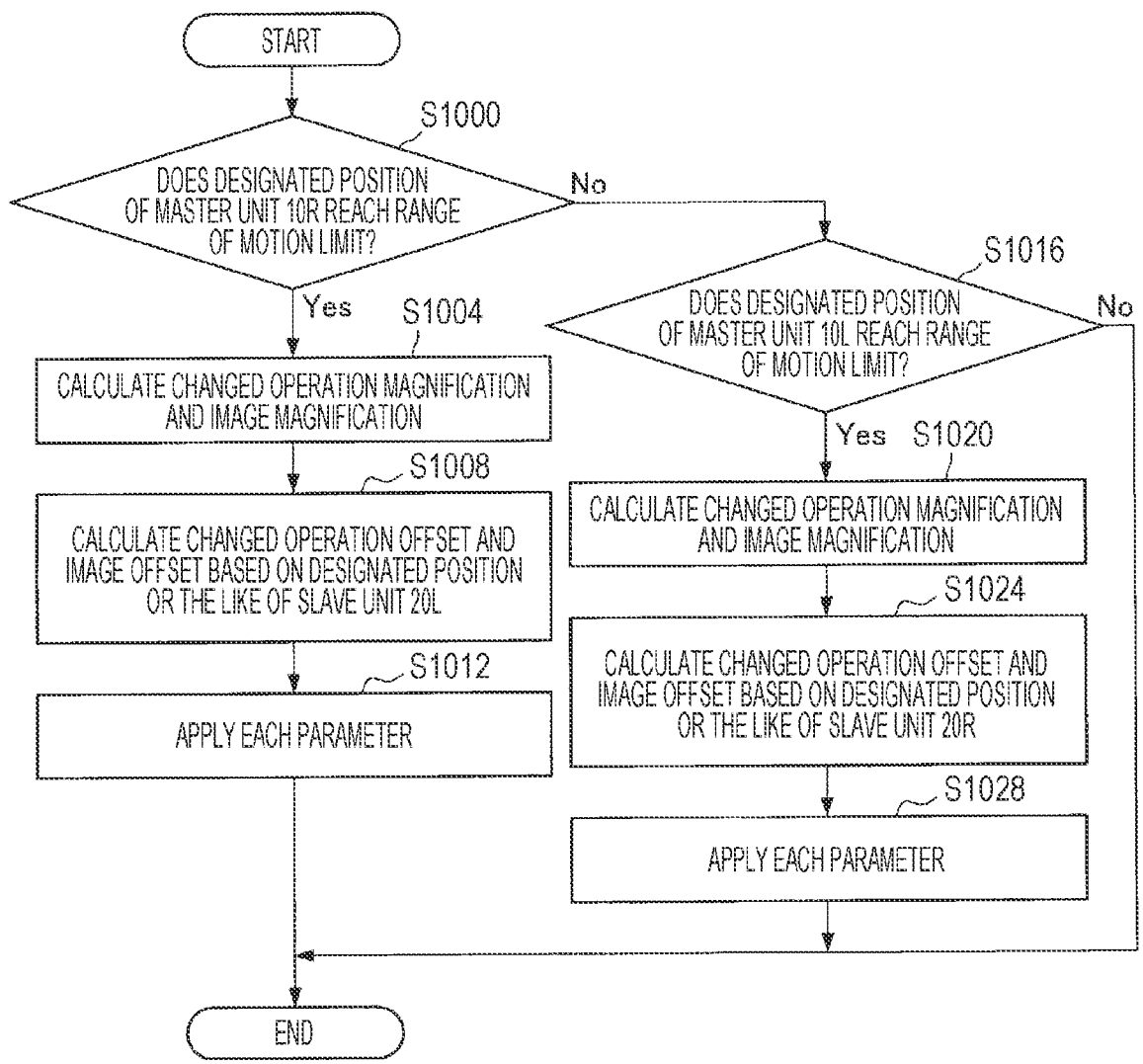
FIG. 11 is a flowchart illustrating an example of a processing flow of the control unit according to the present embodiment.

FIG. 11 is a flowchart illustrating an example of the processing flow of the control unit 50 according to the present embodiment. As an example, FIG. 11 illustrates the processing flow of the reduction control performed by control unit 50 in the case where it is detected that the designated position of master unit 10 has reached the range of motion limit. Note that it is assumed that the first pair of master unit 10 and slave unit 20 is the master unit 10L and the slave unit 20L, and the second pair of master unit 10 and slave unit 20 are the master unit 10R and the slave unit 20R.

In step S1000, the detection unit 510 determines whether or not the designated position of the master unit 10R has reached the range of motion limit on the basis of the information linked by the communication from the master unit 10.

In the case where the designated position of the master unit 10R reaches the range of motion limit (step S1000/Yes), in step S1004, the magnification control unit 520 calculates the operation magnification and the image magnification after the change (after the reduction control).

In step S1008, the offset control unit 530 calculates the operation offset and the image offset after the change (after the reduction control) on the basis of the designated position or the like of the slave unit 20L (including the operation offset before the changing in the operation magnification and the operation magnification before and after the change in the operation magnification).

In step S1012, each parameter (operation magnification, image magnification, operation offset, and image offset) calculated by the magnification control unit 520 and offset control unit 530 is applied. As a result, the control unit 50 can move the designated position of the slave unit 20R while keeping the designated positions of the master unit 10L and the slave unit 20L constant by moving the designated position of the master unit 10R to the range of motion limit. By applying this function, for example, the user can realize the work of pulling the other end of the suture with the slave unit 20R by the desired amount while fixing the end of the suture with the slave unit 20L.

In step S1000, in the case where the designated position of the master unit 10R has not reached the range of motion limit (step S1000/No) and the designated position of the master unit 10L has reached the range of motion limit (step S1016/Yes), in step S1020, the magnification control unit 520 calculates the operation magnification and the image magnification after the change (after the reduction control).

In step S1024, the offset control unit 530 calculates the operation offset and the image offset after the change (after the reduction control) on the basis of the designated position or the like of the slave unit 20R (including the operation offset before the changing in the operation magnification and the operation magnification before and after the change in the operation magnification).

In step S1028, each parameter (operation magnification, image magnification, operation offset, and image offset) calculated by the magnification control unit 520 and offset control unit 530 is applied. As a result, the control unit 50 can move the designated position of the slave unit 20L while keeping the designated positions of the master unit 10R and the slave unit 20R constant by moving the designated position of the master unit 10L to the range of motion limit.

As a result, a series of processes by the control unit 50 is completed. The control unit 50 controls the master-slave system 1 appropriately by repeating the process illustrated in FIG. 11 as needed. Note that in step S1016, the reduction control is not performed in the case (step S1016/No) in which the designated position of the master unit 10L does not reach the range of motion limit.

2.5 Modified Example

In the above, the example of the processing flow by the control unit 50 according to the present embodiment has been described. Subsequently, a modification of the present embodiment will be described.

In the above, in the case where the designated position of the first pair of master unit 10 and slave unit 20 of the two pairs of master unit 10 and slave unit 20 is constant, the control unit 50 changes the designated position of the second pair of master unit 10 and changes the designated position of the second pair of slave unit 20 according to the change in the operation magnification (that is, by applying the operation offset, the second pair of master unit 10 remains stationary and the second pair of slave unit 20 moves). However, as described above, the mode of master-slave control by the control unit 50 is not necessarily limited thereto. For example, in the case where the designated position of the first pair of master unit 10 and slave unit 20 of the two pairs of master unit 10 and slave unit 20 is constant, according to the change in the operation magnification, the control unit 50 according to the modification may keep the designated position of the second pair of slave unit 20 constant and change the designated position of the second pair master unit 10 (that is, by applying the operation offset, the second pair of slave unit 20 may remain stationary and the second pair of master unit 10 may move).

Figure 12:
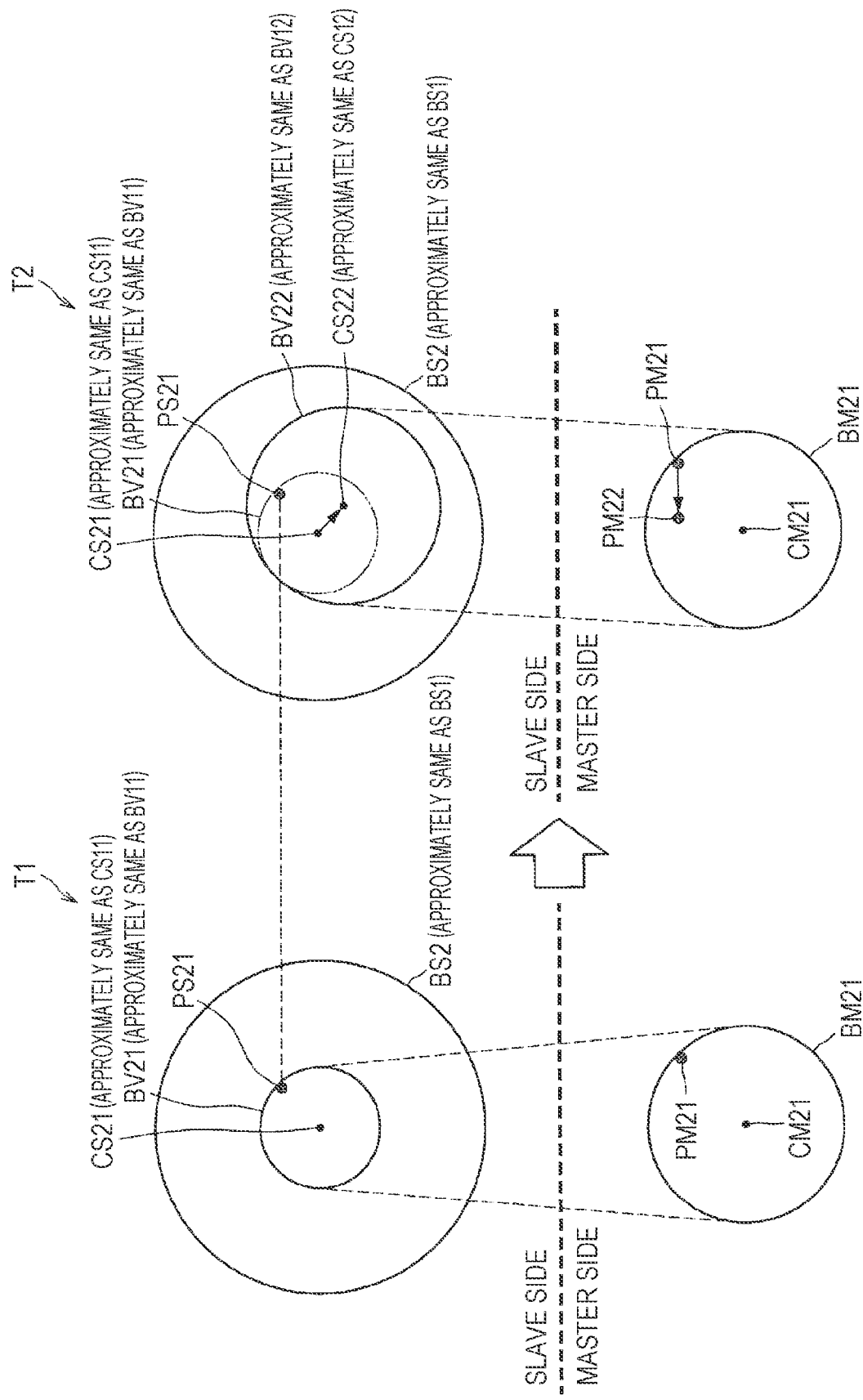
FIG. 12 is a diagram for describing a control example of the second pair of master unit and slave unit according to the change of operation magnification, particularly the reduction in operation magnification in a modification.

FIG. 12 is a diagram for describing an example of controlling the second pair of master unit 10R and slave unit 20R according to the change in the operation magnification, particularly the reduction in the operation magnification in the modification. Note that the control example of the first pair of master unit 10L and slave unit 20L corresponding to FIG. 12 is the same as that illustrated in FIG. 6, and therefore, the description thereof will be omitted.

In FIG. 12, in the state T1 before the reduction of the operation magnification, the center CM21 of the range of motion of the second pair of master unit 10R and the boundary BM21 of the range of motion of the second pair of master unit 10R, a boundary BV21 (approximately the same as the boundary BV11 in FIG. 6) of the operating area of the second pair of slave unit 20R corresponding to the boundary BM21, a center CS21 (approximately the same as the center CS11 in FIG. 6) of the operating area of the second pair of slave unit 20R, a master position PM21 which is the designated position of the second pair of master unit 10R, and the slave position PS21 which is the designated position of the second pair of slave unit 20R according to the master position PM21 are illustrated. In addition, a boundary BS2 (approximately the same as the boundary BS1 in FIG. 6) of the range of motion of the slave unit 20R (particularly the contact portion 211) is also illustrated.

In the case where the state T1 transitions to the state T2 by the reduction control of the control unit 50, the control unit 50 applies the operation offset (operation offset that can keep the master position PM1 and the slave position PS11 in FIG. 6 constant) calculated above. As a result, the center of the operating area moves from the center CS21 to the center CS22 (approximately the same as the center CS12 in FIG. 6). Here, in the modification, the master position PM21 moves to the master position PM22 while the slave position PS21 is kept constant. That is, the master unit 10R moves while the slave unit 20R remains stationary. As a result, as illustrated in FIG. 12, in the state T2, the operating area of the slave unit 20R corresponding to the range of motion of the master unit 10R is larger than the operating area in the state T1, and a boundary BV22 (approximately the same as the boundary BV12 in FIG. 6) of the operating area in the state T2 will be outside the boundary BV21 in the state T1.

With the above reduction control, the control unit 50 can move the second pair of master unit 10R without moving the first pair of master unit 10L and slave unit 20L and the second pair of slave unit 20R.

Note that the mode of the master-slave control is not necessarily limited to the above. For example, in the case where the designated position of the first pair of master unit 10L and slave unit 20L of the two pairs of master unit 10 and slave unit 20 is constant, the control unit 50 according to the modification may change the designated position of both the second pair of master unit 10R and slave unit 20R according to the change in the operation magnification. Further, the image control may be similar to the contents described with reference to FIG. 8, and therefore, the description thereof will be omitted.

2.6. Hardware Configuration Example of Control Unit

Figure 13:
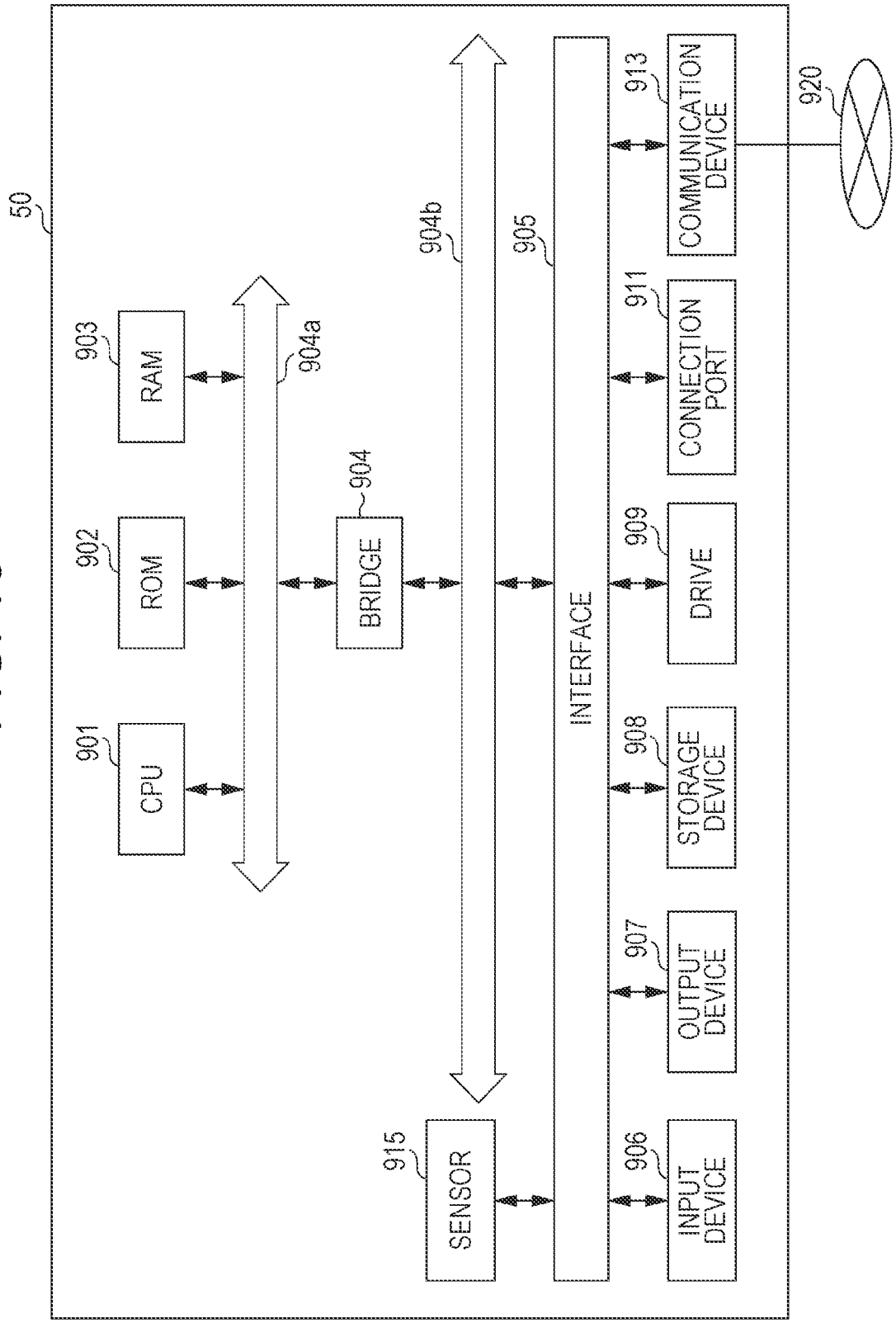
FIG. 13 is a block diagram illustrating a hardware configuration example of the control unit according to the present embodiment.

In the above, the modification of the present embodiment has been described. Subsequently, a configuration example of the hardware according to the present embodiment will be described with reference to FIG. 13. FIG. 13 is a block diagram illustrating a configuration example of the hardware of the control unit 50 according to the present embodiment. The information processing by the control unit 50 according to the present embodiment is realized by the collaboration between the software and the hardware described below.

As illustrated in FIG. 13, the control unit 50 includes a central processing unit (CPU) 901, a read only memory (ROM) 902, a random access memory (RAM) 903, and a host bus 904a. In addition, the control unit 50 includes a bridge 904, an external bus 904b, an interface 905, an input device 906, an output device 907, a storage device 908, a drive 909, a connection port 911, and a communication device 913. The control unit 50 may have a processing circuit such as a DSP or an ASIC, instead of or in addition to the CPU 901.

The CPU 901 functions as an arithmetic processing unit and a control device, and controls all the operations in the control unit 50 according to various programs. In addition, the CPU 901 may be a microprocessor. The ROM 902 stores programs, operation parameters, or the like used by the CPU 901. The RAM 903 temporarily stores programs used in the execution of the CPU 901, parameters that are changed appropriately in the execution, and the like.

The CPU 901, the ROM 902, and the RAM 903 are connected to each other by a host bus 904a including a CPU bus and the like. The host bus 904a is connected to an external bus 904b such as a peripheral component interconnect/interface (PCI) bus via the bridge 904. Note that the host bus 904a, the bridge 904, and the external bus 904b do not necessarily have to be separately configured, and these functions may be mounted on one bus.

The input device 906 is realized by a device, such as a mouse, a keyboard, a touch panel, a button, a microphone, a switch, and a lever, to which information is input by the user. Further, the input device 906 may be, for example, a remote control device using infrared rays or other radio waves, or may be an externally connected device such as a mobile phone or PDA that responds to the operation of the control unit 50. Furthermore, the input device 906 may include, for example, an input control circuit or the like that generates an input signal on the basis of the information input by the user using the above-described input means and outputs the input signal to the CPU 901. By operating the input device 906, the user can input various data to the control unit 50 or instruct the processing operation.

The output device 907 includes a device capable of visually or aurally notifying the user of the acquired information. Such devices include display devices such as a CRT display device, a liquid crystal display device, a plasma display device, an EL display device, and a lamp or audio output devices such as a speaker and a headphone, a printer device, or the like. The output device 907 outputs the results obtained by various processes performed by the control unit 50, for example. Specifically, the display device visually displays the results obtained by various processes performed by the control unit 50 in various formats such as a text, an image, a table, and a graph. On the other hand, the audio output device converts an audio signal including reproduced audio data, acoustic data, etc. into an analog signal and aurally outputs the analog signal.

The storage device 908 is a device for storing data formed as an example of a storage unit that can be provided in the control unit 50. For example, the storage device 908 is implemented by a magnetic storage device such as an HDD, a semiconductor storage device, an optical storage device, a magneto-optical storage device, or the like. The storage device 908 may include a storage medium, a recording device that records data in the storage medium, a reading device that reads data from the storage medium, a deletion device that deletes data recorded in the storage medium, and the like. The storage device 908 stores programs executed by the CPU 901, various data, various data acquired from the outside, and the like.

The drive 909 is a reader/writer for a storage medium, and is built in or externally attached to the control unit 50. The drive 909 reads information recorded in a removable storage medium such as a mounted magnetic disk, optical disk, magneto-optical disk, or semiconductor memory, and outputs the read information to the RAM 903. In addition, the drive 909 can also write information in the removable storage medium.

The connection port 911 is an interface connected to an external device, and is a connection port with an external device capable of transmitting data by, for example, a universal serial bus (USB) and the like.

The communication device 913 is, for example, a communication interface including a communication device or the like for connecting to the network 920. The communication device 913 is, for example, a communication card or the like for wired or wireless local area network (LAN), long term evolution (LTE), Bluetooth (registered trademark), or wireless USB (WUSB). In addition, the communication device 913 may be a router for optical communication, a router for asymmetric digital subscriber line (ADSL), a modem for various kinds of communication, or the like. The communication device 913 can transmit and receive signals and the like to and from, for example, the Internet and other communication devices according to a predetermined protocol such as TCP/IP.

Note that the network 920 is a wired or wireless transmission path of information transmitted from a device connected to the network 920. For example, the network 920 may include a public line network such as the Internet, a telephone line network, and a satellite communication network, various local area networks (LANs) including Ethernet (registered trademark), a wide area network (WAN), and the like. In addition, the network 920 may include a dedicated line network such as an internet protocol-virtual private network (IP-VPN).

The configuration example of the hardware that can realize the function of the control unit 50 according to the present embodiment is illustrated above. Each of the above components may be implemented by using a general-purpose member, or may be implemented by hardware specialized for the functions of each component. Therefore, it is possible to appropriately change the hardware configuration to be used according to the technical level at the time of implementing the present embodiment.

Note that it is possible to create computer programs for implementing each function of the control unit 50 according to the present embodiment as described above, and mount the computer programs on a PC or the like. In addition, it is also possible to provide a computer-readable recording medium in which such a computer program is stored. The recording medium is, for example, a magnetic disk, an optical disk, a magneto-optical disk, a flash memory, or the like. Further, the above computer program may be distributed, for example, via a network without using the recording medium.

3. CONCLUSION

As described above, the control device according to the present embodiment controls the operation offset for two pairs of master unit 10 and slave unit 20 according to the change in the operation magnification in a case where the designated position of the first pair of master unit 10 and slave unit 20 of the two pairs of master unit 10 and slave unit 20 is constant. As a result, the control device according to the present embodiment can be stationary or control the second pair of master unit 10 and slave unit 20 while making the first pair of master unit 10 and slave unit 20 stationary even during the change in operation magnification. Then, the control device according to the present embodiment can prevent the operational errors such as the occurrence of the unintended contact with the affected area, and can continue the operation even during the change in the operation magnification.

As described above, the preferred embodiments of the present disclosure have been described in detail with reference to the accompanying drawings, but the technical scope of the present disclosure is not limited to such examples. It will be apparent to those skilled in the art of the present disclosure that various changes or modifications can be conceived within the scope of the technical idea described in the claims, and it is naturally understood that these changes or modifications fall within the technical scope of the present disclosure.

In addition, the effects described in the present specification are merely illustrative or exemplary, and are not limited to those described in the present specification. That is, the technology according to the present disclosure can exhibit other effects apparent to those skilled in the art from the description of the present specification, in addition to or instead of the effects described above.

Note that the following configurations are also within the technical scope of the present disclosure.

(1)

A control device, including a control unit configured to control an operation offset that indicates a difference between a control reference point for a slave unit and a control reference point for a master unit on the basis of operation magnification indicating a ratio of a movement amount of the master unit to a movement amount of the slave unit, in which the control unit controls the operation offset for two pairs of master unit and slave unit according to a change in the operation magnification in a case where a designated position of a first pair of master unit and a slave unit of the two pairs of master units and the slave units is kept constant.

(2)

The control device described in the (1), in which operating areas of the slave unit in the two pairs of master unit and slave unit are approximately the same.

(3)

The control device described in the (1) or (2), in which the control unit changes a designated position of at least one of a second pair of master unit and slave unit by applying the operation offset.

(4)

The control device described in any one of the (1) to (3), further including a detection unit configured to detect that the designated position of the master unit has reached a range of motion limit, in which in a case where it is detected that the designated position of the master unit has reached the range of motion limit, the control unit performs reduction control to reduce the operation magnification.

(5)

The control device described in the (4), in which the control unit continuously performs the reduction control while it is detected that the designated position of the master unit has reached the range of motion limit.

(6)

The control device described in any one of the (1) to (5), in which the control unit controls image magnification, which is magnification for an image used for the operation of the slave unit, according to the change in the operation magnification.

(7)

The control device described in the (6), in which the control unit controls the operation magnification and the image magnification so that a rate of change of the operation magnification and a rate of change of the image magnification are approximately the same.

(8)

The control device described in any one of claims (1) to (7), in which the control unit further controls an image offset indicating an offset of the image used for the operation of the slave unit according to the control in the operation offset.

(9)

The control device described in the (8), in which the control unit controls the operation offset and the image offset so that a movement direction and a movement amount of the operating area of the slave unit corresponding to the range of motion of the master unit and a movement direction and a movement amount of a display range related to the image are approximately the same.

(10)

A master-slave system, including:

a slave unit;

a master unit used for an operation of the slave unit; and a control unit configured to control an operation offset that indicates a difference between a control reference point for the slave unit and a control reference point for the master unit on the basis of operation magnification indicating a ratio of a movement amount of the master unit to a movement amount of the slave unit, in which the control unit controls the operation offset for two pairs of master unit and slave unit according to a change in the operation magnification in a case where a designated position of a first pair of master unit and slave unit of the two pairs of master units and the slave units is kept constant.

REFERENCE SIGNS LIST

1 Master-slave system
10, 10L, 10R Master unit
20, 20L, 20R Slave unit
30 Display unit
40 Imaging unit
50 Control unit
510 Detection unit
520 Magnification control unit
530 Offset control unit
540 Master-slave control unit
550 Imaging control unit
560 Display control unit

The invention claimed is:

1. A control device, comprising:
a control unit configured to control an operation offset that indicates a difference between a control reference point for a slave unit and a control reference point for a master unit on a basis of operation magnification indicating a ratio of a movement amount of the master unit to a movement amount of the slave unit,
wherein the control unit controls the operation offset for two pairs of master unit and slave unit according to a change in the operation magnification in a case where a designated position of a first pair of master unit and a slave unit of the two pairs of master units and the slave units is kept constant.

2. The control device according to claim 1, wherein operating areas of the slave unit in the two pairs of master unit and slave unit are approximately the same.

3. The control device according to claim 1, wherein the control unit changes a designated position of at least one of a second pair of master unit and slave unit by applying the operation offset.

4. The control device according to claim 1, further comprising
a detection unit configured to detect that the designated position of the master unit has reached a range of motion limit,
wherein in a case where it is detected that the designated position of the master unit has reached the range of motion limit, the control unit performs reduction control to reduce the operation magnification.

5. The control device according to claim 4, wherein the control unit continuously performs the reduction control while it is detected that the designated position of the master unit has reached the range of motion limit.

6. The control device according to claim 1, wherein the control unit controls image magnification, which is magnification for an image used for the operation of the slave unit, according to the change in the operation magnification.

7. The control device according to claim 6, wherein the control unit controls the operation magnification and the image magnification so that a rate of change of the operation magnification and a rate of change of the image magnification are approximately the same.

8. The control device according to claim 1, wherein the control unit further controls an image offset indicating an offset of an image used for the operation of the slave unit according to the control in the operation offset.

9. The control device according to claim 8, wherein the control unit controls the operation offset and the image offset so that a movement direction and a movement amount of an operating area of the slave unit corresponding to a range of motion of the master unit and a movement direction and a movement amount of a display range related to the image are approximately the same.

10. A master-slave system, comprising:
a slave unit;
a master unit used for an operation of the slave unit; and
a control unit configured to control an operation offset that indicates a difference between a control reference point for the slave unit and a control reference point for the master unit on a basis of operation magnification indicating a ratio of a movement amount of the master unit to a movement amount of the slave unit,
wherein the control unit controls the operation offset for two pairs of master unit and slave unit according to a change in the operation magnification in a case where a designated position of a first pair of master unit and a slave unit of the two pairs of master units and the slave units is kept constant.

* * * * *